United States Patent [19]

Stephen

[11] 4,400,169
[45] Aug. 23, 1983

[54] SUBCUTANEOUS PERITONEAL INJECTION CATHETER

[75] Inventor: Robert L. Stephen, Salt Lake City, Utah

[73] Assignee: University of Utah Research Foundation, Salt Lake City, Utah

[21] Appl. No.: 200,830

[22] Filed: Oct. 27, 1980

[51] Int. Cl.$^3$ ............................................. A61M 25/00
[52] U.S. Cl. ........................................ 604/49; 604/93; 604/175; 604/280
[58] Field of Search ....... 128/213 A, 214 R, 348-350; 604/49, 51, 175, 93, 264, 280

[56] References Cited

U.S. PATENT DOCUMENTS

| | | | |
|---|---|---|---|
| 3,633,585 | 1/1972 | McDonald | 128/348 |
| 3,783,868 | 1/1974 | Bokros | 128/348 X |
| 4,160,454 | 7/1979 | Foux | 128/348 |
| 4,184,497 | 1/1980 | Kolff et al. | 128/213 A |
| 4,256,102 | 3/1981 | Monaco | 128/213 A |

OTHER PUBLICATIONS

Boen et al.–Trans. Amer. Soc. Artific. Inter. Orgs., vol. VIII, 1962, pp. 256-262.

*Primary Examiner*—Dalton L. Truluck
*Attorney, Agent, or Firm*—H. Ross Workman; Allen R. Jensen; Berne S. Broadbent

[57] ABSTRACT

A novel implantable, peritoneal injection catheter apparatus and method, the apparatus including an enlarged target surface, fluid-receiving reservoir mounted to one end of a hollow stem. The hollow stem is configured to extend into the peritoneal cavity and includes a retaining ring system for retaining the hollow stem in relationship to the peritoneal cavity. A penetrable membrane covers the enlarged target surface of the receiving reservoir and serves as an injection site for inserting a hollow needle into the receiving reservoir. A substantial portion of the injection catheter is covered with a velour coating to accommodate tissue ingrowth and further securement of the catheter in the tissue of the abdominal wall.

16 Claims, 4 Drawing Figures

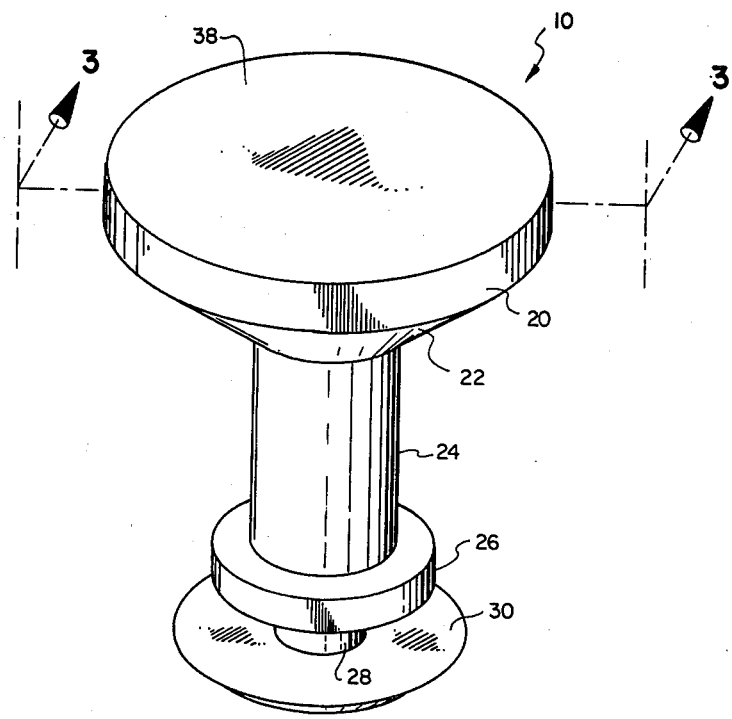
Fig. 2
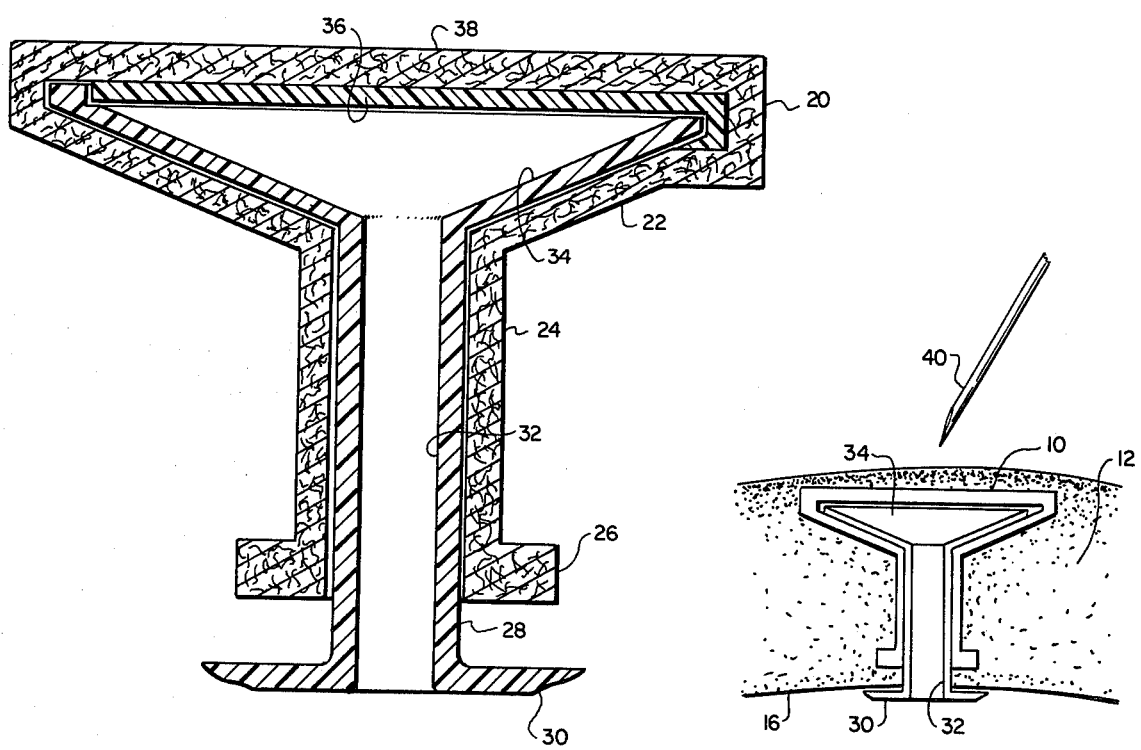
Fig. 3
Fig. 4

SUBCUTANEOUS PERITONEAL INJECTION CATHETER

BACKGROUND

1. Field of the Invention

This invention relates to injection catheters and, more particularly, to a novel subcutaneous peritoneal injection catheter apparatus and method for providing injection access to the peritoneal cavity.

2. The Prior Art

The peritoneum is the largest serous membrane in the body and consists, in the male, of a closed sac, a part of which is applied against the abdominal parietes, while the remainder is reflected over the contained viscera. In the female, the peritoneum is not a closed sac, since the free ends of the uterine tubes open directly into the peritoneal cavity. The part which lines the abdominal wall is named the parietal peritoneum; that which is reflected over the contained viscera constitutes the visceral peritoneum. The space between the parietal and visceral layers of the peritoneum is named the peritoneal cavity; but under normal conditions, this cavity is merely a potential one, since the parietal and visceral layers are in contact.

For a number of years, it has been well-known that the peritoneal membrane will function fairly effectively as an ion exchange membrane for various purposes. As early as 1923, peritoneal dialysis (an artificial kidney format) was first applied clinically. The first peritoneal access device was a piece of rubber tubing temporarily sutured in place. As early as 1960, peritoneal dialysis was becoming an established form of artificial kidney therapy and, in order to lessen the discomfort of repeated, temporary punctures into the peritoneal cavity, various access devices permitting the painless insertion of the acute or temporary peritoneal catheters were developed.

One known peritoneal access device consists of a short, "golf tee" design that is adapted to be placed under the skin with a hollow tubular portion extending just into the peritoneal cavity. This device is designed specifically to allow the insertion of an acute peritoneal catheter (a Trocath) through the skin and down through this access tubing directly into the peritoneal cavity. Another device consists of a catheter buried underneath the skin and extending into the peritoneal cavity via a long tubing. Peritoneal dialysis is performed by inserting a large needle into the subcutaneous portion of the catheter.

All of the devices known were designed with one purpose in view: peritoneal dialysis, and are used almost exclusively by one group of patients, those with End-Stage Renal Disease (ESRD), whose kidney function will never return. In simple terms, therefore, the access devices to the peritoneal cavity plus the peritoneal cavity itself constitute an artificial kidney.

A variety of drugs or other fluids are frequently added to the large volumes of peritoneal dialysis solutions and are thus instilled (injected) into the peritoneal cavity for various therapeutic reasons. Some examples of these drugs are antibiotics, amino acids, and insulin (for diabetics). However, such therapeutic maneuvers are fortuitous in that the clinician is simply taking advantage of a particular situation, that is, a peritoneal access device emplaced in a particular group of patients.

However, there are cogent reasons for not using existing, permanent peritoneal access devices for simple drug injections in a wide variety of patients not suffering ESRD. Most of these devices have what might be termed a relatively large internal volume, that is, it would require anywhere between about five and twenty milliliters, depending upon the device, to fill the device with fluid. This volume which is a dead volume or dead space, is a very real hindrance in that the injected fluid may simply remain within the device itself instead of entering the peritoneal cavity.

In view of the foregoing, it would be an advancement in the art to provide a novel subcutaneous peritoneal injection catheter which may be readily implanted underneath the skin and provide direct access into the peritoneal cavity. It would also be an advancement in the art to provide a subcutaneous peritoneal injection catheter having a relatively small internal volume while providing a relatively enlarged target area. Such a novel subcutaneous peritoneal injection catheter apparatus and method is disclosed and claimed herein.

BRIEF SUMMARY AND OBJECTS OF THE INVENTION

The present invention relates to a novel subcutaneous peritoneal injection catheter apparatus and method, the apparatus including a receiving chamber having a relatively small internal volume while exposing a relatively large target surface area and interconnected with the peritoneal cavity by a hollow stem. A penetrable membrane overlies the receiving chamber to accomodate a hollow needle being inserted into the receiving chamber. Portions of the catheter are covered with a velour surface to accomodate tissue ingrowth and securement of the catheter subcutaneously.

It is, therefore, a primary object of this invention to provide improvements in implantable injection catheters.

Another object of this invention is to provide an improved method for injecting fluids into the peritoneal cavity.

Another object of this invention is to provide a novel subcutaneous peritoneal injection catheter having a relatively small fluid capacity while presenting a relatively large target surface area for a needle to penetrate within the catheter.

Another object of this invention is to provide an implantable injection catheter having securement means for securing the catheter subcutaneously.

These and other objects and features of the present invention will become more fully apparent from the following description and appended claims taken in conjunction with the accompanying drawing.

BRIEF DESCRIPTION OF THE DRAWING

FIG. 2 is a perspective view of a presently preferred embodiment of the novel subcutaneous peritoneal injection catheter of this invention;

FIG. 3 is a cross-section taken along lines 3—3 of FIG. 2; and

FIG. 4 is a fragmentary enlargement of the subcutaneous peritoneal injection catheter of FIG. 1.

DETAILED DESCRIPTION OF THE PREFERRED EMBODIMENTS

Figure 1:
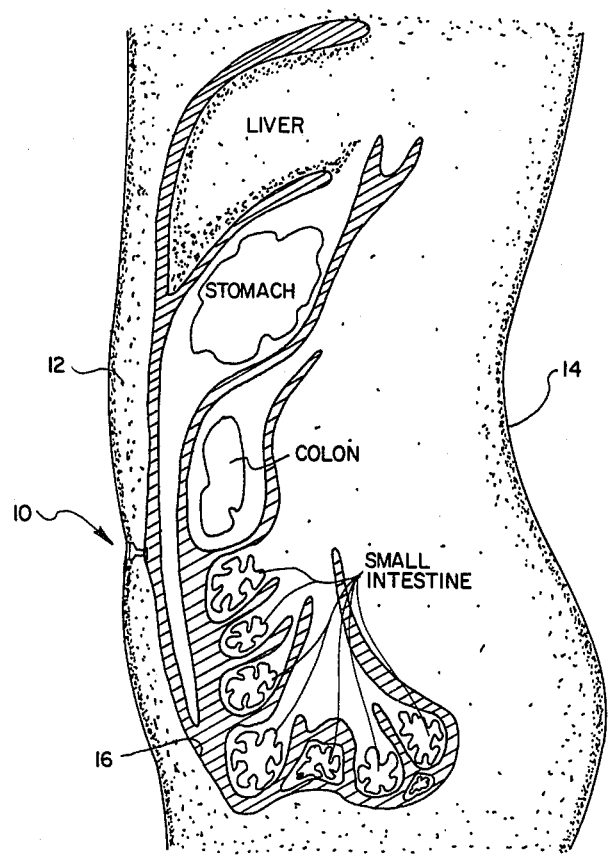
FIG. 1 is a schematic illustration of the novel subcutaneous peritoneal injection catheter of this invention implanted in an abdominal wall.

The invention is best understood by reference to the drawing wherein like parts are designated with like numerals throughout.

GENERAL DISCUSSION

As a general statement, diabetes is generally identified as a metabolic disorder in which the ability to metabolize carbohydrates and, more particularly, glucose, is more or less completely lost due to faulty pancreatic activity and consequent disturbance of normal insulin mechanism. Insulin acts by stimulating the metabolism of glucose, and there is evidence that it does this by facilitating the transport of glucose through the cell membrane. A corollary hormone, glucagon, acts by stimulating the conversion of glycogen into glucose by activating liver phosphorylase. The subsequent release of glucose into the bloodstream causes a hyperglycemic effect which is thus opposite to the hypoglycemic, or bood-sugar-lowering effect, of insulin. It appears that there is a natural balance of action of the two hormones resulting in the control of glucose release and utilization. Insulin is secreted by certain cells of a pancreatic tissue known as the Islets of Langerhans. A deficiency of these cells and consequent decrease in insulin secretion has been found in human subjects who developed diabetes before the age of 23, but many diabetics who first show the disease after maturity have been found to have a considerable amount of insulin in their pancreases, an average of about 50 percent of that for non-diabetics. There is evidence that insulin is more rapidly destroyed by diabetics than by normal subjects. Severe cases of diabetes require insulin treatment, whereas in milder types of diabetics, can frequently be controlled by other means such as diet or certain sulfonamide drugs.

Routine administration of insulin used to treat patients with ketosis-prone diabetes leaves much to be desired. Once or twice daily injections with any of the long-acting insulins, although continuous in a basal sense, makes no pretense at supplying controlled variable amounts of insulin consequent upon charging metabolic demands. Furthermore, aggressive peripheral insulin administration (that is, insulin injected subcutaneously, intramuscularly or intravenously), used in an attempt to obtain tight control of glycemia, may lead to periods of sustained hyperglycemia that occasionally cycles into a hypoglycemic state. It is possible that changes in circulating, metabolically active hormones and/or receptor site concentrations are responsible for this situation.

Possibly the major problem encountered in controlling glycemia in the unphysiological administrative route of therapeutic insulin. The liver, the prime organ involved in regulation of blood glucose levels, is initially bypassed following injection by the peripheral route (subcutaneous, intramuscular, intravenous). Achieving normoglycemia by injection of peripheral insulin inevitably engenders high blood insulin levels (hyperinsulinemia). The physiological insult imposed by hyperinsulinemia perturbs many metabolic feedback loop controls, which in turn lowers the gain of this web of servo mechanisms. The end result is that good sustained control of glycemia is achieved at the expanse of a razor-thin margin between normoglycemia and hypoglycemia. Prolonged hypoglycemia kills people, so diabetologists over the years have generally followed safety-first rules: allow the patient to function in a controlled hyperglycemic state. However, the evidence is now tilting towards a prolonged, if controlled, hyperglycemic state as being at least part of a general metabolic derangement, which causes long-term accelerated vascular and peripheral nerve pathology.

In an effort to regulate these undesirable alternatives (hyperglycemia⇌hypoglycemia), various closed and open loop control delivery systems have been developed. Yet the therapists involved still persist in using these systems to deliver insulin peripherally. Closed loop delivery systems are synonymous with prolonged hospitalization: open loop delivery systems actually produce a more sustained, if somewhat better regulated, hyperinsulinemic state. Additionally, they are awkward to wear, they require tubing sets and implanted needles and, in spite of claims made to the contrary, they can malfunction ("surge"), usually at the most inconvenient hours.

Portal venous administration of insulin has given highly encouraging results in experimental animals: less insulin is required to achieve normoglycemia and hyperinsulinemia is avoided. However, long-term access directly into the portal system carries several severe risks all of which are lethal. Nevertheless, there is a secondary and much safer route leading directly into the portal system: the visceral (that covering most of the gut) peritoneal membrane.

INTRAPERITONEAL INSULIN

Intraperitoneal delivery of insulin has been performed in ketosis-prone diabetic human subjects on a short-term (hours) basis, achieving comparable glycemic control to that achieved with subcutaneous insulin, yet with only approximately half the integrated blood levels of plasma insulin. Intraperitoneal insulin has also been utilized long term in patients with ketosisprone diabetes and end-stage renal disease treated by continuous ambulatory peritoneal dialysis. Adequate control was achieved in the three patients reported.

There is no readily available documentation substantiating the thesis that the intraperitoneal delivery of drugs is primarily absorbed into the portal venous system (visceral peritoneum) rather than the general systemic venous system (parietal peritoneum). However, there is a considerable amount of indirect evidence for this hypothesis: (1) at laparotomy one's field of vision is virtually totally obscured by mesenteric (visceral) peritoneum; (2) the work of other researchers indicates that control of glycemia by intraperitoneal insulin is good yet there was a 50% "loss"—presumably picked up by the liver before reaching the peripheral circulation; (3) intraperitoneal administration of sodium nitroprusside (for the purpose of causing intraperitoneal vasodilatation) resulted in no detectable levels of peripheral plasma thiocyanate: it is assumed that metabolism of nitroprusside by the liver accounted for the lack of peripheral thiocyanate. One researcher stated that he had always presumed intraperitoneal administration of drugs resulted in their direct transfer to the portal venous system but had never tested the hypothesis directly nor could he think of anyone else who had done so.

One final point must be made: Intraperitoneal administration of various dialysis fluids and certain drugs such as antibiotics, permanent access to the peritoneal cavity and knowledge of the physiological migratory route of insulin have been with us for many years. Therefore, why has not intraperitoneal delivery of insulin been utilized in the past? In fact, this route has been used in patients who are diabetic and suffering end-stage renal disease (ESRD). However, until recently, chronic peritoneal dialysis was performed on an intermittent basis (once, twice or thrice weekly), which encouraged only widely spaced use of intraperitoneal insulin. Also, peritoneal dialysate was supplied in glass bottles and insulin sticks to glass in quite substantial amounts. Finally, until recently there were very few diabetic patients treated for ESRD.

The major impediment to utilizing the intraperitoneal route for delivery of insulin in patients not suffering ESRD is lack of a suitable intraperitoneal access device. Standard peritoneal catheters are long, clumsy, percutaneous, infection-prone silastic tubes. One balks at the thought of any patient wearing one of these unless absolutely necessary.

The present invention is a peritoneal access device with the following constraints. (1) The dead space or dead volume of the device is minimal. (2) It presents a large surface area (consistent with the first constraint) to allow for injection of various drugs. (3) It is designed purely and simply for one-way flow, i.e., drug injection is inward only; there is no outflow considered. (4) It is designed so that a variety of drugs may be injected into the peritoneal cavity. (5) It is not designed for peritoneal dialysis and, in fact, would not function if used for this purpose.

THE PREFERRED EMBODIMENT

Referring now more particularly to FIG. 1, the novel implantable, intraperitoneal drug injection catheter is shown generally at 10 implanted in an abdominal wall 12 of a torso 14 to provide access to the peritoneal cavity 16 of torso 14. It is important to emphasize that the peritoneal cavity 16 is shown as though it were partially infused with dialysate. This is done to more clearly set forth the environment of catheter 10.

Referring now more particularly to FIGS. 2-4, catheter 10 is configured with an enlarged head 20 tapering at taper 22 to an elongated, hollow stem 24 having a hollow lumen 32 (FIGS. 3 and 4) extending between a receiving chamber 34 and the peritoneal cavity 16 (FIGS. 1 and 4). The basal framework for catheter 10 includes the frustoconical receiving chamber 34 surmounted to the hollow stem 28 and having a penetrable membrane 36 placed across the enlarged end of frustoconical receiving chamber 34. The lower end of hollow stem 28 terminates in an enlarged, retaining flange 30 for retaining the position of catheter 10 relative to peritoneal cavity 16 and abdominal wall 12 (FIGS. 1 and 4). An outer covering 24 encapsulates catheter 10 and is fabricated from a suitable velour material to encourage tissue ingrowth and fixation in the tissue of abdominal wall 12 (FIGS. 1 and 4).

Catheter 10 is surgically implanted in the abdominal wall in such a position as to provide fluid communication between reservoir 34 and peritoneal cavity 16. Importantly, the enlarged, upper surface area or target 38 is implanted just below the skin surface of abdominal wall 12 so as to provide an enlarged, readily accessible target zone for a hollow needle 40 inserted therethrough into receiving reservoir 34. Fluid injected from hollow needle 40 is received in reservoir 34 and the fluid is transmitted through hollow lumen 32 into peritoneal cavity 16.

Securement of catheter 10 is obtained by initially suturing an enlarged suturing ring 26 of velour covering indirectly to the tissue of abdominal wall 12. Additionally, the retaining ring 30 inhibits dislodgement of catheter 10 from abdominal wall 12 thereby continuously maintaining fluid communication with peritoneal cavity 16.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A subcutaneously implantable injection conduit for injecting a drug into a peritoneal cavity, comprising:
   a hollow receptacle for receiving the drug, the hollow receptacle being formed as an open-top chamber;
   a penetrable membrane over the open top of the chamber;
   a hollow stem having a proximal end and a distal end, the proximal end of the stem being attached to the receptacle such that the stem forms a passageway extending from the chamber, the stem having a length sufficient that the stem penetrates the parietal peritoneal membrane and extends into the peritoneal cavity; and
   a diametrally enlarged flange attached to the stem such that, when the conduit is implanted under a layer of skin adjacent the peritoneal cavity and the flange is secured adjacent the parietal peritoneal membrane, the distal end of the hollow stem is directed toward the mesenteric peritoneal membrane.

2. A subcutaneously implantable injection conduit as defined in claim 1 wherein the receptacle comprises a cavity formed as an inverted, right frustoconical vessel having a diameter greater than depth with the circular base forming the open top of the chamber and connected at the apex of the frustoconical vessel to the hollow stem.

3. A subcutaneously implantable injection conduit as defined in claim 1 wherein the diametrally enlarged flange is attached adjacent the distal end of the hollow stem, the flange thereby inhibiting the stem from retracting into tissue into which the conduit is implanted.

4. A subcutaneously implantable injection conduit as defined in claim 1 further comprising mounting means for mounting the receptacle under a layer of skin adjacent to the peritoneal cavity.

5. A subcutaneously implantable injection conduit as defined in claim 4 wherein the mounting means comprises a velour material covering at least a portion of the injection conduit, the velour material accommodating tissue ingrowth.

6. A subcutaneously implantable injection conduit as defined in claim 4 wherein the mounting means comprises a sewing ring circumscribing the hollow stem, the sewing ring being configured as a flange.

7. A method for injecting a drug into a peritoneal cavity in a direction toward the mesenteric peritoneal membrane, the method comprising the steps of:
   obtaining an injection conduit, comprising:

a shallow vessel with an open top;

a penetrable membrane covering the open top of the vessel;

a hollow stem having a proximal end and a distal end, the proximal end of the stem being attached to the vessel such that the stem forms a passageway extending from the vessel; and a diametrally enlarged flange attached to the stem such that, when the conduit is implanted underneath a layer of skin adjacent the peritoneal cavity and the flange is secured adjacent the parietal peritoneal membrane, the distal end of the hollow stem is directed toward the mesenteric peritoneal membrane;

implanting the injection conduit underneath a layer of skin adjacent the peritoneal cavity with the membrane being generally parallel to the skin, the hollow stem penetrating the parietal peritoneal membrane and extending into the peritoneal cavity, the diametrally enlarged flange being secured adjacent the parietal peritoneal membrane, the distal end of the hollow stem being directed toward the mesenteric peritoneal membrane, and the passageway communicating between the vessel and the peritoneal cavity; and injecting a drug into the peritoneal cavity by penetrating the layer of skin and the penetrable membrane with a hollow needle and forcing the drug through the hollow needle into the vessel with the hollow stem carrying the drug into the peritoneal cavity in a direction toward the mesenteric peritoneal membrane.

8. A method as defined in claim 7 wherein the implanting step further comprises securing the hollow stem in the peritoneal cavity thereby preventing dislodgement of the hollow stem.

9. A method as defined in claim 7 wherein the injection conduit further comprises a velour material encapsulating at least a portion of the vessel, membrane, and stem.

10. A method as defined in claim 7 wherein the drug is insulin and wherein the insulin, upon entering the peritoneal cavity through the hollow stem so as to contact the mesenteric peritoneal membrane, is absorbed into the blood circulation of the portal venous system via said mesenteric peritoneal membrane, whereby the insulin is transported directly to the liver.

11. A subcutaneously implantable injection conduit for injecting a drug into a peritoneal cavity, comprising:

an injection receiver having a diametrally enlarged convergent receiving surface and an opening at the center of the receiving surface;

a diametrally enlarged, penetrable membrane across the receiving surface in spaced relationship therewith, said membrane forming a receiving reservoir in combination with the receiving surface;

mounting means for implanting the conduit under a layer of skin adjacent to the peritoneal cavity;

a hollow stem having a proximal end and a distal end, the proximal end of the stem being attached to the injection receiver such that the stem forms a passageway extending from the opening in the receiving surface, the stem having a length sufficient that the stem penetrates the parietal peritoneal membrane and extends into the peritoneal cavity; and a diametrally enlarged flange attached to the stem such that, when the conduit is implanted under a layer of skin adjacent the peritoneal cavity and the flange is secured adjacent the parietal peritoneal membrane, the distal end of the hollow stem is directed toward the mesenteric peritoneal membrane.

12. A subtcutaneously implantable injection conduit as defined in claim 11 wherein the diametrally enlarged flange is attached adjacent the distal end of the hollow stem, thereby inhibiting the stem from retracting into tissue into which the conduit is implanted.

13. A subcutaneously implantable injection conduit as defined in claim 12 wherein the mounting means comprises a velour material covering at least a portion of the injection conduit.

14. A subcutaneously implantable injection conduit as defined in claim 13 wherein the mounting means further comrises a sewing ring circumscribing the hollow stem and providing a suture site for suturing the sewing ring to adjacent tissue.

15. A subcutaneously implantable injection conduit for injecting insulin into a peritoneal cavity in a direction toward the mesenteric peritoneal membrane, comprising:

an injection receiver having a penetration-resistant, diametrally enlarged, convergent receiving surface and an opening at the center of the receiving surface;

a diametrally enlarged, penetrable cover across the receiving surface in spaced relationship therewith, the cover forming a receiving reservoir in combination with the receiving surface;

a hollow stem having a proximal end and a distal end, the proximal end of the stem being attached to the receiver such that the stem forms a passageway extending from the opening in the receiving surface, and the stem having a length sufficient that, when the injection conduit is implanted in tissue adjacent the peritoneal cavity, the stem penetrates the parietal peritoneal membrane and extends from the injection receiver into the peritoneal cavity; and a diametrally enlarged flange attached adjacent the distal end of the hollow stem such that the flange inhibits the stem from retracting into tissue into which the conduit is implanted, and such that, when the flange is secured adjacent the parietal peritoneal membrane, the distal end of the stem is directed toward the mesenteric peritoneal membrane, whereby the insulin, upon entering the peritoneal cavity through the hollow stem, contacts the mesenteric peritoneal membrane and is absorbed into the blood circulation of the portal venous system via said mesenteric peritoneal membrane, whereby the insulin is transported directly to the liver.

16. A subcutaneously implantable injection conduit as defined in claim 15 further comprising means for mounting the conduit in tissue adjacent the peritoneal cavity, said mounting means comprising a biocompatible velour covering over at least a portion of the external surface of the conduit, the velour covering providing for tissue ingrowth into the velour material.

* * * * *

UNITED STATES PATENT AND TRADEMARK OFFICE
CERTIFICATE OF CORRECTION

PATENT NO. : 4,400,169
DATED : August 23, 1983
INVENTOR(S) : Robert L. Stephen, et al.

It is certified that error appears in the above—identified patent and that said Letters Patent is hereby corrected as shown below:

Title page, in the identification of the inventors, after "Robert L. Stephen," please insert --Carl Kablitz, Barry K. Hanover, Stephen C. Jacobsen, and Jeffrey J. Harrow, all of --

Column 3, line 55, "in" should be --is--

Column 3, line 66, "expanse" should be --expense--

Column 4, line 38, "ketosisprone" should be --ketosis-prone--

Column 8, line 8, (claim 12), "subtcutaneously" should be --subcutaneously--

Column 4, line 67, after "antibiotics," insert --through--

Signed and Sealed this

Seventh Day of February 1984

[SEAL]

Attest:

GERALD J. MOSSINGHOFF

Attesting Officer

Commissioner of Patents and Trademarks